United States Patent
Chenchik et al.

(10) Patent No.: US 6,489,159 B1
(45) Date of Patent: *Dec. 3, 2002

(54) POLYMERIC ARRAYS AND METHODS FOR THEIR USE IN BINDING ASSAYS

(75) Inventors: Alex Chenchik, Palo Alto, CA (US); Paul Siebert, Sunnyvale, CA (US); Michael Herrler, Mountain View, CA (US)

(73) Assignee: Clontech Laboratories, Inc., Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/675,915

(22) Filed: Sep. 29, 2000

Related U.S. Application Data

(63) Continuation-in-part of application No. 09/269,586, filed as application No. PCT/US99/00248 on Jan. 6, 1999, now Pat. No. 6,287,768, which is a continuation-in-part of application No. 09/003,723, filed on Jan. 7, 1998, now Pat. No. 6,087,102.

(51) Int. Cl.[7] ............................. C12M 1/34; C12Q 1/68; C12P 19/34; C07H 21/02; C07H 21/04
(52) U.S. Cl. ......................... 435/287.2; 435/5; 435/6; 435/7.1; 435/91.1; 435/91.2; 536/22.1; 536/23.1; 536/24.3; 536/24.31; 536/24.32; 536/24.33; 530/334; 530/350
(58) Field of Search ..................... 435/5, 6, 7.1, 97.1, 435/91.2; 536/23.1, 24.3, 24.31, 25.4; 530/334, 350

(56) References Cited

U.S. PATENT DOCUMENTS

| | | | |
|---|---|---|---|
| 4,983,044 A | * 1/1991 | Schweber | 356/443 |
| 5,143,854 A | 9/1992 | Pirrung et al. | |
| 5,242,828 A | 9/1993 | Bergstrom et al. | 435/291 |
| 5,242,974 A | 9/1993 | Holmes | 525/54.11 |
| 5,288,644 A | 2/1994 | Beavis et al. | |
| 5,324,633 A | 6/1994 | Fodor et al. | |
| 5,384,261 A | 1/1995 | Winkler et al. | 436/518 |
| 5,405,783 A | 4/1995 | Pirrung et al. | 436/518 |
| 5,412,087 A | 5/1995 | McGall et al. | 536/24.3 |
| 5,424,186 A | 6/1995 | Fodor et al. | 435/6 |
| 5,429,807 A | 7/1995 | Matson et al. | 422/131 |
| 5,432,049 A | 7/1995 | Fischer et al. | |
| 5,436,327 A | 7/1995 | Southern et al. | 536/25.34 |
| 5,445,934 A | 8/1995 | Fodor et al. | 435/6 |
| 5,470,710 A | 11/1995 | Weiss et al. | |
| 5,472,672 A | 12/1995 | Brennan | 422/131 |
| 5,492,806 A | 2/1996 | Drmanac et al. | |
| 5,503,980 A | 4/1996 | Cantor | |
| 5,510,270 A | 4/1996 | Fodor et al. | 435/518 |
| 5,525,464 A | 6/1996 | Drmanac et al. | |
| 5,527,681 A | 6/1996 | Holmes | 435/6 |
| 5,529,756 A | 6/1996 | Brennan | 422/131 |
| 5,545,531 A | 8/1996 | Rava et al. | 435/6 |
| 5,547,839 A | 8/1996 | Dower et al. | |
| 5,554,501 A | 9/1996 | Coassin et al. | 435/6 |
| 5,556,752 A | 9/1996 | Lockhart et al. | 435/6 |
| 5,561,071 A | 10/1996 | Hollenberg et al. | 437/1 |
| 5,580,732 A | 12/1996 | Grossman et al. | |
| 5,599,672 A | 2/1997 | Liang et al. | 435/6 |
| 5,599,895 A | 2/1997 | Heider | |
| 5,610,287 A | 3/1997 | Nikiforov et al. | 536/243 |
| 5,624,711 A | 4/1997 | Sundberg et al. | 427/261 |
| 5,639,603 A | 6/1997 | Dower et al. | 435/6 |
| 5,658,734 A | 8/1997 | Brock et al. | 435/6 |
| 5,658,737 A | * 8/1997 | Nelson et al. | 435/6 |
| 5,661,028 A | 8/1997 | Foote | |
| 5,700,637 A | 12/1997 | Southern | 435/6 |
| 6,087,102 A | * 7/2000 | Chenchik et al. | 435/6 |
| 6,207,810 B1 | * 3/2001 | McClelland et al. | 536/23.1 |

FOREIGN PATENT DOCUMENTS

| | | | |
|---|---|---|---|
| EP | 373 203 | 8/1994 | |
| EP | 0 742 287 A2 | 11/1996 | ............ C12Q/1/68 |
| EP | 785 280 | 7/1997 | |
| EP | 0 799 897 A1 | 10/1997 | ............ C12Q/1/68 |
| WO | 93/17126 | 9/1993 | ............ C12Q/1/68 |
| WO | 95/11995 | 5/1995 | |
| WO | 95/21265 | 8/1995 | |
| WO | 95/35505 | 12/1995 | .......... G01N/33/54 |
| WO | 96/31622 | 10/1996 | |
| WO | 97/10365 | 3/1997 | |
| WO | 97/27317 | 7/1997 | |

OTHER PUBLICATIONS

Clontech Catalog 1995–1996 pp. 55–59 & 140.*

"CLONTECH Innovative Tools To Accelerate Discovery, Multiple Tissue Northern (MTN™)Blots," (1997/1998) *CLONTECH Laboratories, Inc.* p. 81.

"CLONTECH Innovative Tools To Accelerate Discovery, Multiple Tissue Northern (MTN™) Blots," *CLONTECH Laboratories, Inc.*

DeRisi, L. Joseph, et al., "Exploring the Metabolic and Genetic Control of Gene Expression on a Genomic Scale," *Science* (Oct. 24, 1997) vol. 278:680–686.

Glaser, Viki "Rosetta Inpharmatics Chips In," *Nature Biotechnology* (Oct. 15, 1997) vol. 15:937–938.

Hoheisel, D. Jorg "Oligomer–chip Technology," *Tibtech* (Nov. 1997) vol. 15:465–469.

(List continued on next page.)

*Primary Examiner*—Jeffrey Siew
(74) *Attorney, Agent, or Firm*—Bret Field; Bozicevic, Field & Francis LLP

(57) ABSTRACT

Arrays of a plurality of different heterogeneous polymeric target compositions immobilized on the surface of a solid support are provided. In the subject arrays, the constituent polymeric targets of the heterogeneous target compositions are generally biopolymeric compounds, e.g., nucleic acids and proteins, where ribonucleic acids and proteins are the preferred polymeric targets in many embodiments. The subject arrays find use in a variety of different applications, including high throughput gene expression analysis applications.

31 Claims, No Drawings

OTHER PUBLICATIONS

Lockhart, J. David, et al., "Expression Monitoring By Hybridization To High-Density Oligonucleotide Arrays," *Nature Biotechnology* (Dec. 1996) vol. 14:1675–1680.

Marshall, Andrew et al., "DNA chips: An array of possibilities," *Nature Biotechnology* (Jan. 1998) vol. 16:27–31.

Pardee, B. Arthur "Complete genome expression monitoring: The human race," *Nature Biotechnology* (Dec. 1997) vol. 15:1343–1344.

Ramsay, Graham "DNA chips: State-of-the-art," *Nature Biotechnology* (Jan. 1998) vol. 16:40–44.

Saizieu, Antoine et al., "Bacterial transcript imaging by hybridization of total RNA to oligonucleotide arrays," *Nature Biotechnology* (Jan. 1998) vol. 16:45–48.

Sambrook, J., "Molecular Cloning," *A Laboratory Manual*, New York: Second Edition. Cold Spring Harbor Laboratory (1998) vol. 1:7.37–7.52.

Sambrook, J., "Molecular Cloning," *A Laboratory Manual*, New York: Second Edition. Cold Spring Harbor Laboratory (1998) vol. 2:10.27–10.28.

Sambrook, J., "Molecular Cloning," *A Laboratory Manual*, New York: Second Edition. Cold Spring Harbor Laboratory (1998) vol. 3:18.47–18.71.

Shalon, Dari et al., "A DNA Microarray System for Analyzing Complex DNA Samples Using Two-color Fluorescent Probe Hybridization," *Genome Research* (1996) vol. 6:639–645.

Wodicka, Lisa et al., "genome-wide expression monitoring in *Saccharomyces cerevisiae*," *Nature Biotechnology* (Dec. 1997) vol. 15:1359–1367.

* cited by examiner

POLYMERIC ARRAYS AND METHODS FOR THEIR USE IN BINDING ASSAYS

CROSS-REFERENCE TO RELATED APPLICATIONS

This application is a continuation-in-part of application Ser. No. 09/269,586 filed Mar. 30, 2000 now U.S. Pat. No. 6,287,768 Sep. 11, 2001, which is a 371 of PCT/US99/00248, filed Jan. 6 1999; which application is a continuation-in-part of application Ser. No. 09/003,723 filed on Jan. 7, 1998 and now issued as U.S. Pat. No. 6,087,102; the disclosures of which are herein incorporated by reference.

INTRODUCTION

Technical Field

The field of this invention is biopolymeric micro arrays.

BACKGROUND OF THE INVENTION

"Biochips" or micro arrays of binding agents, such as oligonucleotides, have become an increasingly important tool in the biotechnology industry and related fields. These binding agent micro arrays, in which a plurality of binding agents are deposited onto a solid support surface in the form of an array or pattern, find use in a variety of applications, including drug screening, oligonucleotide sequencing, and the like. One important use of biochips is in the analysis of differential gene expression, where the expression of genes in different cells, normally a cell of interest and a control, is compared and any discrepancies in expression are identified. In such assays, the presence of discrepancies indicates a difference in the classes of genes expressed in the cells being compared. Differential gene expression assays allow one to generate expression profiling data for several hundred or even thousand of genes simultaneously for a limited number of biological samples.

However, in certain instances it is desirable to analyze the expression level of a limited number of genes in hundreds or thousands of biological samples simultaneously. For example, such a "reverse approach" would be critical not only for biological samples derived from healthy organisms but also for discovery of novel drug targets and diagnostic markers in large numbers of biological samples derived from different kinds of human pathological samples or model organisms like mouse, rat, etc. which imitate human diseases. The high throughput screening of disease-related biological samples requires the use of large numbers of samples in order to obtain statistically reliable data concerning specificity of gene expression changes in a particular disease state.

As such, there is continued interest in the development of array formats that can provide for high throughput expression analysis in a large number of different biological samples.

RELEVANT LITERATURE

Patents and patent applications describing arrays of biopolymeric compounds and methods for their fabrication include: U.S. Pat. Nos. 5,242,974; 5,384,261; 5,405,783; 5,412,087; 5,424,186; 5,429,807; 5,436,327; 5,445,934; 5,472,672; 5,527,681; 5,529,756; 5,545,531; 5,554,501; 5,556,752; 5,561,071; 5,599,895; 5,624,711; 5,639,603; 5,658,734; WO 93/17126; WO 95/11995; WO 95/35505; EP 742 287; and EP 799 897.

Patents and patent application describing methods of using arrays in various applications include: U.S. Pat. Nos. 5,143,854; 5,288,644; 5,324,633; 5,432,049; 5,470,710; 5,492,806; 5,503,980; 5,510,270; 5,525,464; 5,547,839; 5,580,732; 5,661,028; WO 95/21265; WO 96/31622; WO 97/10365; WO 97/27317; EP 373 203; and EP 785 280.

Other references providing a review of micro array technology, including formats for arrays and methods of their use include: Lockhart et al., Nature Biotechnology (December 1996) 14: 1675.

Clontech Catalogue, 97/98, (Clontech Laboratories, Inc. 1020 East Meadow Circle, Palo Alto Calif. 94303) p. 81 describes premade Northern blots.

SUMMARY OF THE INVENTION

Arrays of a plurality of different heterogeneous polymeric target compositions immobilized on the surface of a solid support are provided. In the subject arrays, the constituent polymeric targets of the heterogeneous target compositions are generally biopolymeric compounds, e.g., nucleic acids and peptides or proteins. The subject arrays find use in a variety of different applications, including high throughput gene expression analysis applications.

Definitions

The term "peptide" as used herein refers to any compound produced by amide formation between a carboxyl group of one amino acid and an amino group of another group.

The term "oligopeptide" as used herein refers to peptides with fewer than about 10 to 20 residues, i.e. amino acid monomeric units.

The term "polypeptide" as used herein refers to peptides with more than 10 to 20 residues.

The term "protein" as used herein refers to polypeptides of specific sequence of more than about 50 residues.

The term "nucleic acid" as used herein means a polymer composed of nucleotides, e.g. deoxyribonucleotides or ribonucleotides.

The terms "ribonucleic acid" and "RNA" as used herein means a polymer composed of ribonucleotides.

The term "mRNA" as used herein refers to only that fraction of the total ribonucleic acids found in a biological source which are capable of being translated into proteins, and therefore includes messenger RNA and polyA+ RNA, but does not include ribosomal RNAs or tRNAs.

The terms "deoxyribonucleic acid" and "DNA" as used herein means a polymer composed of deoxyribonucleotides.

The term "oligonucleotide" as used herein denotes single stranded nucleotide multimers of from about 10 to 100 nucleotides and up to 200 nucleotides in length.

The term "polynucleotide" as used herein refers to single or double stranded polymer composed of nucleotide monomers of generally greater than 100 nucleotides in length.

DESCRIPTION OF THE SPECIFIC EMBODIMENTS

Arrays of a plurality of different heterogeneous polymeric target compositions immobilized on the surface of a solid support are provided. In the subject arrays, the constituent polymeric targets of the heterogeneous target compositions are generally biopolymeric compounds, e.g., nucleic acids and peptides or proteins. The subject arrays find use in a variety of different applications, including high throughput gene expression analysis applications. In further describing the subject invention, the subject arrays will be described first, followed by a review of representative methods of using the arrays and kits for use in practicing such methods.

Before the subject invention is further described, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a," "an," and "the" include plural reference unless the context clearly dictates otherwise. Unless defined otherwise, all technical and scientific terms used herein have the same meaning as commonly understood to one of ordinary skill in the art to which this invention belongs.

Arrays

As summarized above, the subject arrays are arrays of polymeric target compositions that are immobilized on a solid support. The polymeric target constituents of the different polymeric target compositions of the subject arrays, i.e., the individual molecules that make up each target composition on the array, are typically biopolymeric, by which is meant that they are naturally occurring polymeric compounds or at least mimetics or analogues of naturally occurring polymeric compounds. Biopolymeric compounds of particular interest are nucleic acids, including ribonucleic acids, as well as ribonucleic and deoxyribonucleic acid derivatives thereof generated through a variety of processes (usually enzymatic processes) such as reverse transcription, amplification, transcription, etc., e.g. cDNA amplified from RNA (both single and double stranded), cDNA inserts from cDNA libraries, and the like, where in certain embodiments the targets are cDNA molecules generated using the target generation protocols described in U.S. Pat. No. 5,962,272 (e.g., the SMART™ technology) which disclosure is incorporated herein by reference; and peptides, such as oligopeptides, polypeptides and proteins.

In certain preferred embodiments, the polymeric targets are ribonucleic acids. Ribonucleic acids of interest as polymeric targets include total RNA, polyA$^+$RNA, polyA$^-$RNA, snRNA (small nuclear), hnRNA (heterogeneous nuclear), cytoplasmic RNA, pre mRNA, mRNA, cRNA (complementary), and the like. In yet other embodiments, the targets of each of the polymeric target compositions on the array are deoxyribonucleic acids, e.g., cDNA amplified from RNA (both single and double stranded), cDNA inserts from cDNA libraries, and the like, where in certain embodiments the targets are cDNA molecules generated using the target generation protocols described in U.S. Pat. No. 5,962,272 (e.g., the SMART™ technology) which disclosure is incorporated herein by reference. In yet other preferred embodiments, the target constituents of each polymeric target composition on the array are peptides. Peptides of interest as polymeric targets include naturally occurring proteins or fragments thereof, e.g., whole cell or tissue extracts, extracts of particular fractions thereof, such as cytoplasmic proteins, nuclear proteins, extracellular proteins and the like, where such proteins include: antibodies, receptors, hormones, and the like. The peptide/protein targets may be in their native state, or denatured prior to laying down on the substrate surface.

The above described targets may be obtained or derived from naturally occurring biological sources, particularly mammalian sources and more particularly mouse, rat or human sources, where such sources include: fetal tissues, such as whole fetus or subsections thereof, e.g. fetal brain or subsections thereof, fetal heart, fetal kidney, fetal liver, fetal lung, fetal spleen, fetal thymus, fetal intestine, fetal bone marrow; adult tissues, such as whole brain and subsections thereof, e.g. amygdala, caudate nucleus, corpus callosum, hippocampus, hypothalamus, substantia nigra, subthalamic nucleus, thalamus, cerebellum, cerebral cortex, medula oblongata, occipital pole, frontal lobe, temporal lobe, putamen, adrenal cortex, adrenal medula, nucleus accumbens, pituitary gland, adrenal gland and subsections thereof, such as the adrenal cortex and adrenal medulla, aorta, appendix, bladder, bone marrow, colon, colon proximal with out mucosa, heart, kidney, liver, lung, lymph node, mammary gland, ovary, pancreas, peripheral leukocytes, placental, prostate, retina, salivary gland, small intestine, skeletal muscle, skin, spinal cord, spleen, stomach, testis, thymus, thyroid gland, trachae, uterus, uterus without endometrium; cell lines, such as breast carcinoma T-47D, colorectal adenocarcinoma SW480, HeLa, leukemia chronic myelogenous K-562, leukemia lymphoblastic MOLT-4, leukemia promyelocytic HL-60, lung carcinoma A549, lumphoma Burkitt's Daudi, Lymphoma Burkitt's Raji, Melanoma G361, teratocarcinoma PA-1, leukemia Jurkat; and the like. The target, e.g. RNA, may be used directly from its source when present in relatively great abundance or amplified when possible/desired, e.g. by PCR, transcription or cloning procedures, where necessary, e.g. when relatively rare, such as RNA from rare tissue, etc.

Where the targets are derived from naturally occurring sources, such as mammalian tissues as described above, the targets may be derived from the same or different organisms. As such, in certain embodiments the targets that make up each of the different compositions displayed on the array surface are derived from the same organism. In other embodiments, the targets that make up each of the different compositions displayed on the array surface are derived from different organisms.

In addition, the target samples arrayed on the plate can be derived from normal and disease or condition states of the same organism or multiple organisms, like cancer, stroke, heart failure, aging, infectious diseases, inflammation, exposure to toxic, drug or other agents, conditional treatment, such as heat shock, sleep deprivation, physical activity, etc., different developmental stages, and the like.

In certain embodiments, the plurality of different target compositions that is displayed on the surface of the array, i.e., the set of different target compositions of the array, includes at least one normal/disease pair, where the number of different normal/disease pairs of target compositions present on the array may be much greater, and in many embodiments is at least 5, usually at least 10 and more usually at least 20, where the number may be 50, 100, 200 or higher, depending on the particular array. By "normal/disease pair of target compositions" is meant a collection or set of two or more different target compositions which includes at least one target composition derived from a normal tissue and at least one target composition derived from a disease tissue. In other words, in any given set or collection of target compositions that make up a normal/disease pair of target compositions, at least one target composition will be a composition obtained from a normal sample and at least one target composition will be a composition obtained from a disease sample. As such, any given normal/disease pair of target compositions includes, at a minimum two different compositions—one normal and one disease. In certain embodiments, a given normal/disease pair of target compositions includes more than one disease and/or target composition, where in these embodiments, the number of different disease compositions in the pair ranges from about 20 to 10,000, usually from about 50 to 5,000 and more usually from about 100 to 2,000, where the number is, in many embodiments, a number that provides for a statistically relevant number of samples displayed on the array, by which is meant at least 5 disease compositions for each type of disease displayed on the array. The number of different diseases displayed on the array can be as great as about 1000 or greater, but usually is less than about 300 and more usually less than about 100. The subject arrays can include one particular type of disease on the array or several different types of diseases. The number of control or normal samples or compositions in a given pair may range from about 2 to 500 usually from about 10 to 100. In those embodiments where a given normal/disease pair includes two or more different disease target compositions, the different disease compositions of the pair all represent the same disease, e.g., they are taken from multiple different organisms all suffering from the same disease, such that only one disease is represented in any given normal/disease pair of target compositions. The normal/disease pair can be derived from the same tissue/cell type or from different tissue/cell types for each particular disease state. In general, normal target is derived from a healthy organism, i.e., one that does not have any symptoms of disease, particularly the disease with which it will be paired. The number of normal target compositions is usually less than the number of disease targets, and may be at least 2, usually at least 5 and more usually at least 10, but can be 50 or higher.

The normal/disease pairs described above may represent a variety of different diseases. Diseases of interest include: (a) Infectious and Parasitic Diseases, e.g., Intestinal Infectious Diseases, i.e. Cholera, Typhoid Fever, Salmonella Infections; Tuberculosis; Bacterial Diseases, i.e. Diphtheria; Human Immunodeficiency Virus (HIV) Infection; Poliomyelitis; Viral Diseases, i.e. Herpes Simplex, Measles, Rubella, Yellow Fever; Viral Hepatitis; Arthropod-Bome Diseases, i.e. Malaria; Venereal Diseases, i.e. Syphilis; Mycoses; (b) Neoplasms, e.g., Malignant Neoplasms; Benign Neoplasms; Carcinoma in situ; (c) Endocrine, Nutritional, and Metabolic Diseases and Immunity Disorders; e.g., Diabetes Mellitus, subtypes; Thiamine and Niacin Deficiency States, i.e. Beriberi; Vitamin Deficiency States; Disorders of Amino-Acid Transport and metabolism, i.e. Phenylketonuria; (d) Diseases of the Blood and Blood-Forming Organs, e.g., Anemias; Thalassemias; Coagulation Defects, i.e. Factor VIII Deficiency, von Willebrand's Disease; Systemic Lupus Erythematosis; Leucemia, ie. Acute Promyelocytic Leucemia; Chronic Myeloleukemia; Lymphogranulomatasis; Lymphoblastosis; Hemophilia A and B; Autoimmune Thrombocytopenia; (e) Mental Disorders, e.g., Psychoses, i.e. Dementia; Arteriosclerotic Dementia; Alcoholic Psychoses; Drug Psychoses; Alzheimer Disease; Epilepsy; Huntington's Disease; Jacob-Creutzfeldt Disease; Multiple Sclerosis; Schizophrenia; Neurotic Disorders, i.e. Anxiety, Multiple Personality, Phobic Disorders; Neurosis; (f) Diseases of the Nervous System and Sense Organs; Inflammatory Diseases, i.e. Meningitis, Encephalitis; Gaucher Disease; Alzheimer's Disease; Parkinson's Disease; (g) Diseases of the Circulatory System and Cardiovascular Diseases; Arthritis; Rheumatic Fever; Rheumatic Heart Disease; Hypertensive Diseases; Ischemic Heart Disease, i.e. Arteriosclerosis; Arteritis; Cardiomyopathy; Dysfunction of Glucose Metabolism; Dysfunction of Cellular Iron Channels; Dysfunction of Lipid Metabolism; (h) Diseases of the Respiratory System, e.g., Bronchitis; Pneumonia and Influenza; (i) Diseases of the Digestive System, e.g., Ulcer; Gastritis; Necrosis; Chronic Liver Diseases and Cirrhosis, i.e. Chronic Hepatitis; (j) Diseases of the Genitourinary System, i.e., Prostatitis; Benign Mammary Dysplasias, i.e. Fibrosclerosis; (k) Diseases of the Skin and Subcutaneous Tissue, e.g., Cellulitis; Dermatitis; (l) Diseases of the Musculoskeletal System and Connective Tissue; e.g., Systemic Lupus erythematosus; Arteriosclerosis; Arthritis; Osteoarthrosis; etc.

In the subject arrays, the targets are stably associated with the surface of a solid support. By stably associated is meant that the targets maintain their position relative to the support surface under hybridization and washing conditions. In other words, the targets are immobilized on the support (i.e., substrate) surface. The targets can be non-covalently or covalently stably associated with the rigid support surface. Examples of non-covalent association include non-specific adsorption, specific binding through a specific binding pair member covalently attached to the support surface, and entrapment in a matrix material, e.g., a hydrated or dried separation medium, which presents the target in a manner sufficient for binding, e.g. hybridization, to occur. Examples of covalent binding include covalent bonds formed between the target and a functional group present on the surface of the rigid support, e.g., —OH, where the functional group may be naturally occurring or present as a member of an introduced linking group, as described in greater detail below.

The solid support may be a rigid or flexible support or substrate. Therefore, in certain embodiments the solid support of the array is a rigid substrate. By rigid is meant that the support is solid and does not readily bend, i.e. the support is not flexible. Examples of solid materials which are not rigid supports with respect to the present invention include membranes, flexible plastic films, and the like. As such, the rigid substrates of the subject arrays are sufficient to provide physical support and structure to the polymeric targets present thereon under the assay conditions in which the array is employed, particularly under high throughput handling conditions.

The rigid substrates of the subject arrays may be fabricated from a variety of materials. The materials from which the substrate is fabricated should ideally exhibit a low level of non-specific binding of probe during hybridization or specific binding events. In many situations, it will also be preferable to employ a material that is transparent to visible and/or UV light. Specific materials of interest include: glass; plastics, e.g. polytetrafluoroethylene, polypropylene, polystyrene, polycarbonate, and blends thereof, and the like; metals, e.g. gold, platinum, and the like; etc.

As indicated above, in other embodiments of the subject invention, the substrates or supports are flexible. By flexible is meant that the support is capable of being bent, folded or similarly manipulated without breakage. Examples of solid materials which are flexible solid supports with respect to the present invention include membranes, e.g., nylon membranes, flexible plastic films, and the like.

The substrates upon which the subject patterns of targets are presented in the subject arrays may take a variety of configurations ranging from simple to complex, depending on the intended use of the array. Thus, the substrate could have an overall slide or plate configuration, such as a rectangular or disc configuration, where an overall rectangular configuration, as found in standard microtiter plates and microscope slides, is preferred. Generally, the length of the rigid substrates will be at least about 1 cm and may be as great as 40 cm or more, but will usually not exceed about 30 cm and may often not exceed about 15 cm. The width of rigid substrate will generally be at least about 1 cm and may be as great as 30 cm, but will usually not exceed 20 cm and will often not exceed 10 cm. The height of the rigid substrate will generally range from 0.01 mm to 10 mm, depending at least in part on the material from which the rigid substrate is fabricated and the thickness of the material required to provide the requisite rigidity. The substrate can be used directly in hybridization assays or can be used in a cartridge or chips, e.g., it can be surrounded by a rigid material, like plastic, for easy manipulation during hybridization, washing and collection steps.

The substrate of the subject arrays comprises at least one surface on which a pattern of target compositions is present, where the surface may be smooth or substantially planar, or have irregularities, such as depressions or elevations. The surface on which the pattern of target compositions, e.g., spots, is presented may be modified with one or more different layers of compounds that serve to modulate the properties of the surface in a desirable manner. Such modification layers, when present, will generally range in thickness from a monomolecular thickness to about 1 mm, usually from a monomolecular thickness to about 0.1 mm and more usually from a monomolecular thickness to about 0.001 mm. Modification layers of interest include: inorganic and organic layers such as metals, metal oxides, polymers, small organic molecules and the like. Polymeric layers of interest include layers of: peptides, proteins, polynucleic acids or mimetics thereof, e.g. peptide nucleic acids and the like; polysaccharides, phospholipids, polyurethanes, polyesters, polycarbonates, polyureas, polyamides, polyethyleneamines, polyarylene sulfides, polysiloxanes, polyimides, polyacetates, and the like, where the is polymers may be hetero- or homopolymeric, and may or may not have separate functional moieties attached thereto, e.g. conjugated.

As mentioned above, each different target composition on the arrays is a heterogeneous mixture of different molecules, e.g., nucleic acids, proteins, etc., where the number of different or distinct molecules present in a given target composition is generally at least about 100, usually at least about 1000 and more usually at least about 5,000. Any two molecules are considered different or distinct if they have a molecular structure that differs, e.g., they differ from each other by nucleotide or amino acid sequence. The mass of each different target composition on the array may range from about 1 pg to 10 $\mu$g, usually from about 100 pg to 5 $\mu$g and more usually from about 1 ng to 1 $\mu$g.

In certain embodiments, the masses of all of the target compositions on the array are substantially the same. In other words, the amount of material that makes up each of the different target compositions on the array is substantially the same. In yet other embodiments, the target compositions on the array are normalized. By normalized is meant that the amount of each target composition on the array is selected to provide for normalization. By normalization is meant that the amount of targets in each target composition is selected to provide for a known relationship of expression of at least one housekeeping gene in two or more of the target compositions, including all or a substantial subpopulation of the target compositions. As such, the amount of each target composition on the array may be chosen to provide for an expression signal that is substantially equal in each spot for at least one housekeeping gene. Alternatively, the amount may be chosen to provide for known ratios of signals with respect to the at least one housekeeping gene. In certain embodiments, all of the different target compositions on the array may be normalized with respect to each other. In yet other embodiments, two or more subsets or populations of the target compositions may be normalized with respect to all of the members within the set, but not to other members in other set(s). For example, where the array includes a normal/disease pair which includes a plurality of normal target compositions and a plurality of disease target compositions, all of the normal target compositions may be normalized with respect to each other and all of the disease target compositions may be normalized with respect to each other. In another embodiment, if the array includes normal/disease pairs derived from different tissues, all the normal/disease pairs belonging to the same tissue may be normalized to each other and other normal/disease pairs will be normalized separately. The normalized amounts of each target composition may be chosen using any convenient protocol. Methods of identifying/determining normalized amounts of target are well known to those of skill in the art and any convenient protocol may be employed, where particular protocols of interest may be based on one or a plurality of different housekeeping genes, where when a plurality of housekeeping genes are employed, the number of different housekeeping genes may be at least 5, at least 10 or higher. Alternatively, a normalization protocol for reading the array in which the amount of each target composition is not normalized may be employed, where this normalization protocol is described in greater detail under the heading "Normalization" infra.

As summarized above, the subject arrays comprise a plurality of different polymeric targets, where the number of targets is at least 5, usually at least 8, and may be much higher. In some embodiments, the arrays have at least 10 distinct spots, usually at least about 20 distinct spots, and more usually at least about 50 distinct spots, where the number of spots may be as high as 10,000 or higher. In yet other embodiments, the number of different spots is at least 100, where the number may range from about 100 to 2,000 or more. The density of the spots on the solid surface in certain embodiments is at least about 5/cm$^2$ and usually at least about 50/cm$^2$ but does not exceed about 1000/cm$^2$, and usually does not exceed about 500/cm$^2$, where in certain embodiments the density may range from about 300 to 400/cm$^2$.

The arrays of the subject invention may be used directly in binding assays using well known technologies, e.g., contacting with probe in a suitable container, under a coverslip, etc, or may be incorporated into a structure that provides for ease of analysis, high throughput, or other advantages, such as in a biochip format, a multiwell format and the like. For example, the subject arrays could be incorporated into a biochip type device in which one has a substantially rectangular shaped cartridge comprising fluid entry and exit ports and a space bounded on the top and bottom by substantially planar rectangular surfaces, wherein the array is present on one of the top and bottom surfaces.

Alternatively, the subject arrays could be incorporated into a high throughput or multi-well device, wherein each array is bounded by raised walls in a manner sufficient to form a reaction container wherein the array is the bottom surface of the container. Representative high throughput devices that may be modified to incorporate arrays of the subject invention are described in U.S. patent application Ser. No. 5,545,531, the disclosure of which is herein incorporated by reference. Generally in such devices, the devices comprise a plurality of reaction chambers, each of which contains the array on the bottom surface of the reaction chamber. By plurality is meant at least 2, usually at least 4 and more usually at least 24, where the number of reaction chambers may be as high as 96 or higher, but will usually not exceed 100. The volume of each reaction chamber may be as small as 10 µl but will usually not exceed 500 µl. In a preferred embodiment, the volume is between about 50 and 200 µl.

An important feature of the subject invention is that the arrays of the present invention are characterized by having at least one of a rigid solid support and/or at least one normal/disease pair of polymeric target compositions.

Array Preparation

The subject arrays may be prepared as follows. The substrate or support can be fabricated according to known procedures, where the particular means of fabricating the support will necessarily depend on the material from which it is made. For example, with polymeric materials, the support may be injection molded, while for metallic materials, micromachining may be the method of choice. Alternatively, rigid supports such as glass, plastic, or metal sheets can be purchased from a variety of commercial sources and used. The surface of the support may be modified to comprise one or more surface modification layers, as described above, using standard deposition techniques.

The next step in the preparation process is to prepare the target compositions and then stably associate or immobilize the target compositions onto the surface of the support. The complex source of target molecules that make up each target composition may be obtained from a naturally occurring physiological source using standard techniques. Protocols for isolating nucleic acids, proteins and their fractions from cells, tissues, organs and whole organisms are described in: Maniatis et al., Molecular Cloning: A Laboratory Manual (Cold Spring Harbor Press)(1989); Scope R., Protein Purification. Principle and Practice (Springer-Verlag)(1994); and Deutscher, Guide to Protein Purification (Academic Press) (1990). Such methods typically involve subjection/treatment of the original biological source to one or more of tissue/cell homogenization, nucleic acid/protein extraction, chromatography, centrifugation, affinity binding and the like. Target molecule composition preparation can further include one or more treatments designed to provide for one or more of the following: more stable association with the surface of the rigid support; better hybridization and detection; etc. Such treatments will necessarily depend on the nature of the target molecules being prepared, but may include one or more of: reverse transcription; nuclease treatment; protease digestion; in vitro transcription; in vitro translation; DNA amplification; enzymatic or chemical modification of RNA or proteins, such as the introduction of functional moieties, such as biotin, digoxigenin, fluorescent moieties, antigens, chelator groups, chemically active or photoactive groups, etc.; and the like.

Following preparation of the plurality of different complex mixtures of the target molecules, each mixture is stably associated with, i.e., immobilized on, the surface of the support. Any convenient protocol for immobilizing the complex mixtures on the support surface can be employed. Examples of non-covalent association include non-specific adsorption, binding based on electrostatic interactions (e.g. ion-pair interactions), hydrophobic interactions, hydrogen bonds, specific binding through a specific binding pair member covalently attached to the support surface, and the like. Examples of covalent binding include covalent bonds formed between the spotted nucleic acids and a functional group present on the surface of the rigid support, e.g. —OH, where the functional group can be naturally occurring or present as a member of an introduced linking group; etc. Following stable placement of the pattern of target molecules on the support surface, the resultant array may be used as is or incorporated into a biochip, multiwell or other device, as describe above, for use in a variety of binding applications.

The subject arrays or devices into which they are incorporated may conveniently be stored following fabrication for use at a later time. Under appropriate conditions, the subject arrays are capable of being stored for at least about 6 months and may be stored for up to one year or longer. The subject arrays are generally stored at temperatures between about −20° C. to room temperature, where the arrays are preferably sealed in a plastic container, e.g. bag, and shielded from light.

Utility

Applications in which the subject arrays find particular use are expression analysis applications. Such applications generally involve the following steps: (a) preparation of probe; (b) contact of probe with the array under conditions sufficient for probe to bind with corresponding target, e.g. by hybridization or specific binding; (c) removal of unbound probe from the array; and (d) detection of bound probe. Each of these steps will be described in greater detail below.

How the probe is prepared will necessarily depend on the specific nature of the probe, e.g. whether the probe is nucleic or peptidic. For nucleic acid probes, the probes may be ribo- or deoxyribonucleotides, as well as hybridizing analogues or mimetics thereof, e.g. nucleic acids in which the phosphodiester linkage has been replaced with a substitute linkage, such as a phosphorothioate, methylimino, methylphosphonate, phosphoramidite, guanidine and the like; and nucleic acids in which the ribose subunit has been substituted, e.g. hexose phosphodiester, peptide nucleic acids; locked nucleic acids; and the like. The probe will have sufficient complementarity to its target to provide for the desired level of sequence specific hybridization. Where the probe is a nucleic acid, the length of the probe will generally range from about 10 to 2000 nt, where oligonucleotide probes will generally range in length from about 15 to 100 nt and polynucleotide probes will generally range in length from about 100 to 1000 nt, where such probes may be single or double stranded, but will usually be single stranded, e.g., in a sense or antisense orientation related to the corresponding sequence of the target on the array. The nucleic acid probes finding use in the subject methods may be synthesized using known chemical or enzymatic synthesis technologies, cloning procedures or obtained from a natural source. Where the assay protocol employs a single label, it is preferred that a single test probe that hybridizes to one gene of interest is employed. In multiplex approaches, several test probes may be employed so long as they are distinguishably labeled, where the number of different test probes may be at least 2 to 3, but generally does not exceed from about 10 to 20.

Peptidic probes that find use in the subject invention include: antibodies, e.g. polyclonal, monoclonal, and binding fragments thereof; peptides with high affinity to the target, as well as analogues and mimetics thereof; ligands, receptors, and the like. As with the nucleic probes, peptidic probes may be obtained from naturally occurring sources or synthesized using available technologies.

Generally, the probe molecule will be labeled to provide for detection in the detection step. By labeled is meant that the probe comprises a member of a signal producing system and is thus detectable, either directly or through combined action with one or more additional members of a signal producing system. Examples of directly detectable labels include isotopic and fluorescent moieties incorporated into, usually covalently bonded to, a moiety of the probe, such as a nucleotide monomeric unit, e.g. dNMP of the primer, or a photoactive or chemically active derivative of a detectable label which can be bound to a functional moiety of the probe molecule. Isotopic moieties or labels of interest include $^{32}$P, $^{33}$P, $^{35}$S, $^{125}$I, and the like. Fluorescent moieties or labels of interest include coumarin and its derivatives, e.g. 7-amino-4-methylcoumarin, aminocoumarin, bodipy dyes, such as Bodipy FL, cascade blue, fluorescein and its derivatives, e.g. fluorescein isothiocyanate, Oregon green, rhodamine dyes, e.g. Texas red, tetramethylrhodamine, eosins and erythrosins, cyanine dyes, e.g. Cy3 and Cy5, macrocyclic chelates of lanthanide ions, e.g. quantum dye™, fluorescent energy transfer dyes, such as thiazole orange-ethidium heterodimer, TOTAB, etc. Also of interest are nanometer sized particle labels detectable by light scattering, e.g. "quantum dots." Labels may also be members of a signal producing system that act in concert with one or more additional members of the same system to provide a detectable signal. Illustrative of such labels are members of a specific binding pair, such as ligands, e.g. biotin, fluorescein, digoxigenin, antigen, polyvalent cations, chelator groups and the like, where the members specifically bind to additional members of the signal producing system, where the additional members provide a detectable signal either directly or indirectly, e.g. antibody conjugated to a fluorescent moiety or an enzymatic moiety capable of converting a substrate to a chromogenic product, e.g. alkaline phosphatase conjugate antibody; and the like. Additional labels of interest include those that provide for signal only when the probe with which they are associated is specifically bound to a target molecule, where such labels include: "molecular beacons" as described in Tyagi & Kramer, Nature Biotechnology (1996) 14:303 and EP 0 070 685 B1. Other labels of interest include those described in U.S. Pat. No. 5,563,037; WO 97/17471 and WO 97/17076.

The next step in the subject method is to contact the probe with the array under conditions sufficient for binding between the probe and the target of the array. For example, where the probe and targets are nucleic acids, the probe will be contacted with the array under conditions sufficient for hybridization to occur between the probe and target, where the hybridization conditions will be selected in order to provide for the desired level of hybridization specificity. For peptidic probes, conditions will be selected to provide for specific binding between the probe and its target.

Contact of the array and probe involves contacting the array with an aqueous medium comprising the probe. Contact may be achieved in a variety of different ways depending on specific configuration of the array. For example, where the array simply comprises the pattern of size separated targets on the surface of a "plate-like" rigid substrate, contact may be accomplished by simply placing the array in a container comprising the probe solution, such as a polyethylene bag, small chamber, and the like. In other embodiments where the array is entrapped in a separation media bounded by two rigid plates, the opportunity exists to deliver the probe via electrophoretic means. Alternatively, where the array is incorporated into a biochip device having fluid entry and exit ports, the probe solution can be introduced into the chamber in which the pattern of target molecules is presented through the entry port, where fluid introduction could be performed manually or with an automated device. In multiwell embodiments, the probe solution will be introduced in the reaction chamber comprising the array, either manually, e.g. with a pipette, or with an automated liquid handling device.

In certain embodiments, the array is also contacted with one or more, usually no more than four and more usually no more than three, where the number is often 1 or at most 2, reference/control probes. The reference/control probes may be labeled that same as the test probe, or they may be distinguishably labeled, e.g., a different fluorescent color, where when they are distinguishably labeled, one has the opportunity to contact the array with the test and reference/control probe(s) at the same time. Use of reference/control probes provides for, among other things, normalization of the signal observed for the test probe, as described in greater detail infra.

Contact of the probe solution and the targets will be maintained for a sufficient period of time for binding between the probe and the target to occur. Although dependent on the nature of the probe and target, contact will generally be maintained for a period of time ranging from about 10 min to 24 hrs, usually from about 30 min to 12 hrs and more usually from about 1 hr to 6 hrs.

Following binding of probe and target, the resultant hybridization patterns of labeled probe may be visualized or detected in a variety of ways, with the particular manner of detection being chosen based on the particular label of the nucleic acid, where representative detection means include scintillation counting, autoradiography, fluorescence measurement, colorimetric measurement, light emission measurement and the like.

The method may or may not further comprise a non-bound label removal step prior to the detection step, depending on the particular label employed on the probe. For example, in homogenous assay formats a detectable signal is only generated upon specific binding of probe to target. As such, in homogenous assay formats, the hybridization pattern may be detected without a non-bound label removal step. In other embodiments, the label employed will generate a signal whether or not the probe is specifically bound to its target. In such embodiments, the non-bound labeled probe is removed from the support surface. One means of removing the non-bound labeled probe is to perform the well known technique of washing, where a variety of wash solutions and protocols for their use in removing non-bound label are known to those of skill in the art and may be used. Alternatively, in those situations where the targets are entrapped in a separation medium in a format suitable for application of an electric field to the medium, the opportunity arise to remove non-bound labeled probe from the target by electrophoretic means.

The above methods can be varied to provide for multiplex analysis. For example, one can employ a plurality of different probe molecules that are each distinguishably labeled, e.g. with different fluorophores.

The above assays can be used to determine both the expression level of the target bound by the probe. The target expression level in the particular tissue being analyzed can be derived from the intensity of the detected signal. To ensure that an accurate level of expression is derived, a housekeeping gene of known expression level can also be detected, e.g. using a multiplex approach as described above, to provide for a control signal level in order to calibrate the detected probe signal.

As such, the subject arrays find use in a variety of different gene expression analysis applications, including differential expression analysis of diseased and normal tissue, e.g. neoplastic and normal tissue; different tissues or subtypes; tissues and cells under different condition states, like predisposition to disease, age, exposure to pathogens or toxic agents, etc.; and the like.

Normalization

In certain embodiments, the above described methods further include use of a normalization protocol. This particular normalization protocol provides a method for normalizing relative amounts of target compositions, e.g., samples (such as nucleic acids derived from an RNA sample, as described above), by employing an integral factor that is determined based on a set of internal reference ribonucleic acids. The reference ribonucleic acids, e.g., housekeeping genes, used to generate the integral factor are preferably expressed in all cells with medium to high relative abundance and possess low or moderate tissue to tissue variability. Once determined, the integral factor allows a relative determination of integral or total transcript levels in a sample based on the levels of one or more of the reference ribonucleic acids in the sample. Based on the measured expression level of test mRNA, the level of any reference mRNA, and the integral factor, the procedure allows one to normalize the expression level of test mRNAs between multiple samples. This procedure allows the determination of the relative level of a test transcript between samples without being dependent of the actual levels of total RNA assayed, thus obviating the requirement for normalization of total mRNA amount prior to loading multiple samples onto an array. Preferably, the selected reference nucleic acids are housekeeping gene products (or transcripts), and more preferably the reference nucleic acids of a selected set belong to different functional classes of genes.

This particular normalization protocol provides a systematic, reliable and reproducible method for normalizing test mRNA levels between different total RNA samples without regard to the actual amount of RNA sample used for detection (RNA sample is equivalent to an RNA target composition of the subject arrays). The present invention employs an integral factor for mathematical "normalization" between RNA samples, which is determined based on a set of reference RNAs. The reference RNAs are sequences expressed in all cells with medium to high relative abundance, and which possess low or moderate sample to sample variability in case they are derived from the same biological species. The integral factor is determined based on the levels of the reference RNAs in a sample, and is used to quantitate levels of other transcripts on the array based on detected levels of one or more of the reference RNAs.

This procedure allows the determination of the relative level of a test mRNA in each RNA sample without the requirement for normalization of total RNA sample amount prior to loading multiple RNA samples on an array using the level of reference RNA and integral factor as a guideline. Preferably, the selected reference RNAs correspond to housekeeping genes, and more preferably the reference RNAs of a set belong to different functional classes of housekeeping genes.

The integral factor for any RNA sample used for normalizing the amount of total RNA sample is determined by comparison of levels of a set of reference RNAs from that sample. In the method of the invention, at least six reference RNAs are used in each set for normalizing levels of total RNA between samples. Multiple reference RNAs are used to determine the integral factor to minimize the effects of expression level variation of each reference RNA between different cell/tissue types or between different healthy and diseased individuals. By using a variety of reference RNAs instead of a single mRNA to normalize levels of total RNAs between samples, it is also possible to minimize non-specific variations in expression that can be observed in different hybridization experiments, different sample preparations, etc.

For example, expression of test mRNA isolated from the same tissue sample, but isolated in separate preparations, can be normalized by determining an integral factor that will account for the differences in methodology. Integral factors can also be determined for identifying equivalent amounts of RNA from size-selected fractions of different RNA samples from a single preparation. An integral factor can be determined to normalize total RNA or test mRNA in two or more different tissue types in different physiological states, e.g. liver tissue and smooth muscle, different tissues in development, aging, etc. An integral factor can be determined to normalize differences in expression in the same underlying tissue type at different disease/pathological stages, e.g. an adenomatous polyp and a colorectal carcinoma in comparison with normal control tissue. In another example, an integral factor can be determined to normalize expression levels in the same tissue type from different individuals, e.g. pathologically "normal" pancreas tissue from individual A and individual B. The integral factor can be used to normalize RNA samples isolated from treated or exposed cells, tissues, organisms, i.e. hypoxia, heat shock, drug treatment, physical activity, diet, etc.

The set of reference RNAs all have certain characteristics that make them desirable for determination of the integral factor: 1) they are expressed in substantially all cells with a relatively constant abundance and possess low or moderate tissue to tissue variability; 2) the different reference RNAs used within a single set preferably encode proteins belonging to at least three different functional classes; 3) the reference RNAs usually have transcript sizes between 1 to 3 kilobases, as ribonucleic acids of this size provide a sharp hybridization signal in Northern blot analysis. These reference RNAs, when used as a set, help to eliminate specific variation of expression between tissue/cell types that may be present using only one or a few reference RNAs.

To determine an integral factor for a sample, different total RNA samples or nucleic acids derived from RNA, e.g., SMART™ amplified cDNA target (in preferred embodiment poly A+ RNAs) are spotted on a series of flexible supports (i.e. membranes) or solid supports (i.e. glass) in a known gram amount. Each flexible or solid support of the series preferably contains the same amount and spot pattern of poly A+ RNAs. Each spotted array is then hybridized with one or more gene-specific control/reference probes (in preferred embodiment—one) for a potential reference RNA target. Generally, the probe will be labeled either directly or through combined action with one or more additional members of a signal producing system. Examples of directly detectable labels include isotopic and fluorescent moieties incorporated into, usually covalently bonded to, a moiety of the probe, such as a nucleotide monomeric unit, or a photoactive or chemically active derivative of a detectable label, which can be bound to a functional moiety of the probe molecule. Isotopic moieties or labels of interest include $^{32}$P, $^{33}$P, and the like. Fluorescent moieties or labels of interest include coumarin and its derivatives, fluorescein and its derivatives, rhodamine dyes, cyanine dyes, Alexa dyes, Bodipy dyes and the like, etc. For multiplex analysis one can employ a plurality of different probe molecules that are each distinguishable labeled, e.g. with different fluorescent fluorophores.

Following binding of labeled control/reference probe to target ribonucleic acid, the resultant hybridization patterns of labeled targets can be visualized or detected in a variety of ways, with the particular manner of detection being chosen based on the particular label of the nucleic acid, where representative detection means include autoradiography, fluorescence measurement, or light emission measurement and the like. Usually, the hybridization signal is quantitated using phosphorimaging technology. At this stage of the procedure it should be already clear which reference RNAs give minimal signal variation between different cells/tissues, and which should be considered as standards for the best determination of the integral factor.

An average signal is calculated for each tissue/cell, pooling the data from those potential reference RNAs that are considered to be useful for determination of the integral factor. In the next step the quantities for each tissue/cell sample necessary to produce equal average signal is calculated. For example, if some RNA samples show 2-fold less average signal intensity than others, the calculated (adjusted) amount of RNA for these samples will be 2-fold more than for others. The original RNA sample amounts are adjusted to reflect the fluctuations in the relative average signal intensity for the next round of spotting.

The subsequent round of determining the integral factor will be carried out with generally between 20 and 6, but not less than 3, selected reference ribonucleic acids (e.g. the ribonucleic acids that display the best signal and consistency between tissues). The process is repeated as described above, with different adjusted amounts of total RNA spotted on supports and each array hybridized with a probe for a specific reference RNA from the set. These finally chosen reference RNAs are used for the mathematical calculation of the integral factor.

The integral factor for mathematically normalizing a set of samples is calculated using the following procedure:

First, a set of arrays with known gram quantities of each RNA sample, and more preferably identical array with each RNA sample in a specific position on the support, are assayed for levels of the reference RNAs in preferred embodiment. Each support is probed with a single labeled control/reference probe, and the amount of signal of this reference RNA is determined for each RNA sample on the support. Thus, for each RNA sample (R1, R2, etc.) a quantified signal is measured ($S_{R1}$, $SR_{R2}$, etc.). The signal is preferably measured using a phosphor imager, but can also be measured using other techniques known in the art.

Second, the percentage (P) of signal that each RNA sample contributes to the sum of all signals on the array is calculated for each hybridization (or for each reference RNA). For example, this can be determined by the equation:

$$P = (S/\Sigma) \times 100$$

where P is the percentage of the signal, S is the measured intensity of the single signal (e.g., $S_{R1}$), and $\Sigma$ is the level of all measured signals of the different RNA samples on the support ($S_{R1}+S_{R2}+S_{R3}+ \ldots$). This percentage (P) is determined for each RNA sample on each array, resulting in a single sample (e.g., R1) having a P value for each array assayed, i.e. a P value for each reference ribonucleic acid.

Third, the sum (H) of all of the P values for a particular RNA sample on all of the assayed arrays is calculated. For example, H can be calculated for sample R1 by adding the P values for R1 from each array assayed. Some P values, which show obvious tissue or cell-specific variation for some tissues/cells, could be excluded from sum calculation. Usually, the P value could be rejected if it shows more than 3-fold, more commonly 5-fold, and most commonly 10-fold variation from the average P value for a particular tissue across all reference RNAs. For example, β-actin reference RNA usually shows about 5-fold higher signals in skeletal muscle and heart than in other tissues, which reflects high level of muscle-specific expression of actin isoform.

An integral factor can then be determined for each RNA sample by a calculation in which the integral factor (IF) is arbitrarily set to 1 for a single RNA sample. The integral factor can be determined for the other RNA samples to allow a relative determination of mRNA levels between the samples. For example, if the level of sample R1 was set to 1, the integral factor for each of the other samples (e.g. R2 and R3) can be determined using the following equation:

$$IF_{R1} = H_{R1}/H_{R1} = 1$$

$$IF_{R2} = H_{R1}/H_{R2}$$

$$IF_{R3} = H_{R1}/H_{R3}$$

The whole calibration process described above can be repeated to ensure accuracy of the calculated integral factor, and the numbers compared for accuracy and/or averaged for more consistent results. Preferably, at least two rounds are performed to determine the IF for each sample. In another embodiment the integral factor can be calculated by using other well known in art algorithms, for example developed for calculation of NASDAQ or DOW JONES indexes. In such approach, for any particular tissue the P values calculated for each reference RNA are used directly to calculate sum. An additional coefficient k reflects accuracy and significance of P value measurement. Accuracy and significance for each reference RNA depends on tissue to tissue variation and relative signal intensities, reproducibility from experiment to experiment, etc. The formula for sum calculation for RNA sample 1 looks like:

$$H1 = P_1 \cdot k_1 + P_2 \cdot k_2 + P_3 \cdot k_3 + \ldots P_n \cdot k_n$$

In most cases, k is equal or less than 1, usually between 1 and 0.1, more usually between 1 and 0.3, and most commonly between 1 and 0.5.

Once the integral factor has been calculated for all RNA samples used, it can be used to normalize the amount of spotted RNA samples in order to achieve equal average intensity of hybridization signals from all tested reference RNAs. Such produced array based on normalized amount of spotted RNA samples can be used directly for comparing normalized expression levels of any test mRNA. In this approach, a labeled gene-specific cDNA fragment or oligonucleotide specific for the test mRNA is hybridized with the normalized RNA array. The intensity of the hybridization signal can be directly used to compare the expression level of the test mRNA in different tissues/cells.

If the RNA amounts in an equivalent gram amount of each sample are to be compared, a signal obtained for test mRNA in each RNA sample is multiplied by the IF to determine the normalized levels of the test mRNA in each sample. Thus, if an array contains RNA samples R1, R2 and R3, and each sample is present in a 1 gram quantity, the normalized expression levels of a test RNA can be determined by multiplying the signal intensity of each sample with the integral factor for that sample.

In another example, if test mRNA expression levels are to be compared in different amounts of each RNA sample, the signal generated from a labeled test probe is first adjusted to reflect the difference in the gram amounts of each RNA sample, and then the relative levels of test mRNA present in each sample are determined using the integral factor. Thus, if an array contains RNA samples R1, R2 and R3, and the samples are present in a 1, 2 and 6 grams quantity, respectively, the detected signals for test mRNA are first adjusted to reflect the actual levels: the signal of R1 is multiplied by 6, the signal of R2 is multiplied by 3, and signal of R3 is left as is. Once the test mRNA signals have been altered to reflect for amounts of sample, the relative levels of signal generated by the test probe in each sample can be determined by multiplying the signals with its respective integral factor.

For instance, if there is relatively little of sample Ri available, a smaller gram quantity of R1 can be spotted on an array with sample R2 and the integral factor determined for these samples can be used to provide a meaningful comparison of test mRNA levels between R1 and R2. In another example, if a RNA sample has a very high or very low amount of transcription, various levels of a single RNA sample can be compared to another sample, and the relative levels determined using the calculated integral factor.

In preferred embodiment instead of using the integral factor for normalizing the amount of signal for test mRNA the invention disclosed to use the absolute level of any reference RNA used in order to calculate the integral factor. Once the integral factor for each RNA is calculated based on a set of selected reference RNAs, each signal intensity (S) described above for each reference RNA is proportional (and described by formulas above) to the integral factor of all reference RNA set. It means, that if you know the absolute intensity of hybridization signals generated by any reference RNA (used in a set), signal generated by test mRNA and integral factor for each RNA sample on array is enough in order to normalize expression level of test mRNA between all RNA samples. The invention discloses that the first step in preferred protocol will be to perform the hybridization assay with two hybridization probes (sequentially or mixed together in hybridization assay) designed for reference RNA and test mRNA. Then based on intensities of hybridization signals for test mRNA, reference RNA, and value of integral factor the normalized expression level of test mRNA will be calculated using the integral factor. This protocol does not require performing multiple hybridizations with several reference RNAs for each array type and each RNA sample. As soon as the integral factor is calculated for each RNA sample, the normalization of test mRNA expression level between RNA samples requires only one single hybridization with any reference RNA. In preferred embodiment there can be one reference RNA, in some cases it can be two or three, but not more than 6 and in most cases less than 4. Using a single reference RNA signal as internal standard for calculating normalized expression level of test RNA allow to adjust (compensate) variation generated by inaccuracy in spotting technology (i.e. differences in amount of spotted RNA), differences in quality (total mRNA amount in RNA sample preparation) of RNA sample, variation in hybridization, washing, detection conditions, etc.

A number of different ribonucleic acids can be used to determine the integral factor. For example, a number of housekeeping genes were tested for use as reference ribonucleic acids. Ubiquitin (2.3 kilobases), phospolipase A2 (2.8 kilobases), and 23 kDa highly basic protein (0.7 kilobases) belong to multigene families and generate multiple bands on a Northern Blot. The intensity of the major mRNA sizes in brackets may therefore vary in different tissues and cell types. β-tubulin (1.6 kilobases), hypoxanthine guanine phosphoribosyl transferase (HPRT) (1.3 kilobases), ribosomal protein S9 (RPS9) (0.7 kilobases), and ornithine decarboxylase (2.5 kilobases) on the other hand are only moderately abundant. Other reference ribonucleic acids can also be used, as will be apparent to one skilled in the art upon reading the present disclosure. Alternatively, 18S and 28S rRNAs can be used as internal standards. The expression level of these rRNAs is less likely to fluctuate under conditions that affect the expression of mRNAs, because they are transcribed by a distinct polymerase.

Kits

Also provided are kits for performing binding assays using the subject arrays, where kits for carrying out differential gene expression analysis assays are preferred. Such kits according to the subject invention will at least comprise an array according to the subject invention, where the array may simply comprise a pattern of target compositions on a planar support or be incorporated into a multiwell configuration, biochip configuration, or other configuration. The kits may further comprise one or more additional reagents for use in the assay to be performed with the array, where such reagents include: probe generation reagents, e.g. buffers, primers, enzymes, labels and the like; reagents used in the binding step, e.g. hybridization buffers; signal producing system members, e.g. substrates, fluorescent-antibody conjugates, etc.; control probes, e.g., pre-labeled control probes; washing and/or hybridization containers; and the like.

Finally, systems which incorporate the subject arrays, particularly the biochip and multiwell configurations of the subject arrays, are provided, where the systems find use in high throughput gene expression analysis in which information regarding the expression level a gene in a tissue is desired. By the term "system" is meant the working combination of the enumerated components thereof, which components include those components listed below. Systems of the subject invention will generally comprise the array, a fluid handling device capable of contacting the probe fluid and all reagents with the pattern of target molecules on the array and delivery and removing wash fluid from the array surface; a reader which is capable of providing identification of the location of positive probe target binding events and the intensity of the signal generated by such binding events; and preferably a computer means which capable of controlling the actions of the various elements of the system, i.e. when the reader is activated, when fluid is introduced and the like.

The following examples are offered by way of illustration and not by way of limitation.

Experimental

EXAMPLE 1

Preparation and Use of RNA Chip

A. Pin Spotting of Poly A+ RNAs on a Solid Support

A set of different poly A+ RNAs, usually between 8 and 100, are spotted on a solid glass support. The poly A+ RNAs are stably associated with the glass surface through covalent binding. Several methods may be employed for the attachment of nucleic acids, i.e. DNA or RNA, to glass. For example, aliphatic amino groups are introduced to the surface of glass slides by reaction with aminopropyl silane. Poly A+ RNAs pretreated with 10 M sodium isothiocyanate (NaNCS) solution (1:1) are then pin spotted onto the aminopropyl modified glass surface by a Biomek 2000 (Beckmann) robot. The binding occurs through amino-reactive phenylisothiocyanate groups. The poly A+ RNAs are photo-crosslinked to further ensure stable association with the surface of the glass support. In addition, the glass slides are incubated for 2 hours at 80° C. Alternatively, an amino derivatized glass surface is coupled to p-phenylenediisothiocyanate (PDC) to convert the amino groups to amino-reactive phenylisothiocyanate groups.

Nucleic acids are then reacted with their amino groups and the second isothiocyanate group in PDC to yield surface bound DNA or RNA. The reaction is carried out in 0.5-M sodium carbonate buffer, pH: 9.1. After UV-crosslinking either aminopropyl modified or PDC modified glass slides are washed in ddH$_2$O at 95° C. for 5 min. To avoid background signals after hybridization the glass slides are blocked for 15 min with 100 mM glycine solution. Then glass slides are rinsed with ddH$_2$O and ethanol. After incubation for 15 min at 37° C. the slides are ready for use in hybridization experiments.

B. Hybridization, X-ray Detection or Fluorescence Detection

The glass slides with immobilized poly A$^+$ RNAs produced as described above are incubated with 5 ml of CLONTECH's "ExpressHybridization" solution (Clontech, Palo Alto, Calif.) mixed with either radiolabeled or fluorescein-labeled cDNAs. The hybridization temperature is 50° C. Incubation occurs overnight. The glass slides are washed twice with 2×SSC, 0.1% SDS solution for 10 min. at room temperature, once with 1×SSC, 0.1% SDS solution for 5 min. at 68° C., and once with 0.1×SSC for 5 min. at room temperature. Finally, the glass slides are rinsed with sterile filtered water for about 1 min. Hybridization signals are detected using either a phosphor imager in the case of emission of radioactive signals or a fluoroimager (Molecular Dynamics) in the case of emission of fluorescent signals.

EXAMPLE 2

Preparation and Use of Tumor/Normal Matched Pairs Array

Identifying molecular markers for cancer has become an important aim for cancer therapy and a critical goal for successful treatment. Molecular markers for cancer can be identified by monitoring the expression of thousands of genes using cDNA microarrays, differential display, and subtractive hybridization. However, it is often difficult to acquire the amount of RNA required for these methods from small clinical samples such as needle biopsies and microdissected tumors. These small tissues are becoming more common in clinical research, and, as a result, there is an increasing need for methods that amplify limiting amounts of RNA, while maintaining the representation profile of the original RNA. SMART PCR-generated cDNA accurately represents the original mRNA population, producing specific and quantitative signals during membrane hybridization. To determine if SMART cDNA could be used to detect differentially expressed genes in cancer tissues, we arrayed normalized SMART cDNA generated from matched tumor and normal tissues onto nylon membranes.

SMART™ PCR cDNA Synthesis

Total RNAs of matched tumor and normal tissues from kidney, breast, prostate, uterus, ovary, cervix, colon, lung, stomach, rectum, and small intestine were reverse-transcribed using the SMART™ PCR cDNA Synthesis Kit (CLONTECH Laboratories, Palo Alto, Calif., USA) according to the user manual, with some modifications. Briefly, 1 μg of total RNA was mixed with 1 μl of 10 μM oligo(dT) (CDS primer), 1 μl of 10 μM SMART II Oligonucleotide, and deionized water for a total volume of 5 μl. For annealing, this mixture was heated at 72° C. for 2 min, cooled on ice for 2 min, and spun briefly. The reaction was followed by the addition of 2 μl of 5×Reaction Buffer (250 mM Tris-HCl, pH 8.3; 30 mM MgCl$_2$ and 375 mM KCl), 1 μl of 20 mM dithiothreitol (DTT), 1 μl of 10 mM dNTP (10 mM each of dATP, dCTP, dGTP, dTTP) (Amersham Pharmacia Biotech, Piscataway, N.J., USA), 0.5 μl of 100 U/μl of PowerScript™ reverse transcriptase (CLONTECH Laboratories, Palo Alto, Calif., USA), and 0.5 μl of 28 U/μl ANTI-RNase™ (Ambion, Austin, Tex., USA). Samples were incubated at 42° C. for 1 hr in an air incubator, followed by inactivation of RT at 72° C. for 7 min. Then 40 μl of TE buffer (10 mM Tris HCl, pH 7.4, 1 mM EDTA) was added to each sample, which was subsequently stored at −20° C. To determine the number of PCR cycles necessary for optimal amplification of cDNA, 1 μl from each first-strand cDNA reaction mixture was combined with 10 μl of 10×Advantage Polymerase Buffer (40 mM Tricine-KOH, pH 9.2; 15 mM KOAc; 3.5 mM Mg(OAc)$_2$), 1 μl of PCR primer (5'-AAGCAGTGGTAAC-AACGCAGAGT-3'), 2 μl of 10 mM dNTP (10 mM each of dATP, dCTP, dGTP, dTTP), and 1 μl of the Advantage™ cDNA Polymerase Mix (CLONTECH Laboratories, Palo Alto, Calif., USA). Samples were then amplified in an MJ Research thermocycler (MJ Research, Watertown, Mass., USA) using the following program: 1 cycle at 95° C. for 1 min, then 15 cycles at 95° C. for 15 sec, 65° C. for 30 sec, and 68° C. for 6 min. After 15 cycles, 15 μl of the reaction mixture was transferred to a fresh 0.5-ml tube and subjected to 3 additional cycles, while the remaining 85 μl of the PCR mixture was kept at 4° C. After 3 additional cycles, 5 μl of reaction mixture was aliquoted for gel-analysis while the remaining 10 μl of the reaction mixture was subjected to another 3 cycles for a total of 21 cycles. To determine the optimal number of cycles, 5 μl of each of the reaction mixture (i.e., 15-, 18- and 21-cycle PCR products) was analyzed on a 1.1% agarose gel in Tris-Acetate EDTA (TAE) buffer. Based on results of the agarose gel analysis, samples were subjected to additional cycles as necessary.

Preparation of cDNA Array Membranes cDNAs were purified using the NucleoTrap® PCR Purification Kit (CLONTECH Laboratories, Palo Alto, Calif., USA) and eluted in 55 μl of TE buffer. One microgram of total RNA yields up to 10 μg of purified SMART cDNA. Pre-normalized cDNA arrays were prepared by spotting 50 ng of cDNA on Nytran Nylon membranes (Schleicher and Schuell, Keen, N.H., USA) in a 96- or 384-well format using a BIOMEK® 2000 laboratory automation workstation (Beckman Instruments, Fullerton, Calif., USA). Each pair of matched tumor and normal cDNA was then normalized independently as follows. Three arrayed membranes were probed separately with the following housekeeping genes: ubiquitin (UBI), ribosomal protein S9 (RPS9), and 23 kD highly basic protein (23 kD). The hybridization signals were quantified by phosphorimaging. The percentage (P) that each cDNA sample in a pair contributed to the sum of the signals of both members of the pair was calculated for all three housekeeping genes. An integral factor (IF) was calculated for each matched pair by dividing the sum of the percentages of signal intensity for normal cDNA dots ($P_{N\text{-}UBI}+P_{N\text{-}23\ kD}+P_{N\text{-}RPS9}$) by the sum of the percentages of signal intensity for matching tumor cDNA dots ($P_{T\text{-}UBI}+P_{T\text{-}23\ kD}+P_{T\text{-}RPS9}$). The calculated integral factor was then used to raise or decrease the amount of either normal or tumor cDNA to achieve a comparable value for both dots.

Normalized amounts of cDNAs were then spotted on nylon membranes along with nine cancer cell line cDNAs (50 ng/spot); negative controls (50 ng/spot) including yeast total RNA (NC-1), yeast tRNA (NC-2), *E. coli* DNA (NC-3), poly r(A) (NC-4), human C$_o$t-1 DNA (NC-5), and human genomic DNA (NC-6); and ubiquitin cDNA (10 ng/spot) as a positive control.

Hybridization of cDNA Arrays cDNA probes were labeled using DECAprime™ II DNA labeling kit (Ambion, Austin, Tex., USA) and [α-$^{32}$P] dATP (Amersham Pharmacia Biotech, Piscataway, N.J., USA) according to the user manual.

cDNA membranes were prehybridized and then hybridized overnight at 68° C. with radiolabeled cDNA probes in a hybridization bottle containing ExpressHyb™ Hybridization Solution (CLONTECH Laboratories, Palo Alto, Calif., USA), 100 μg/ml sheared salmon sperm DNA, and 1–2×10$^6$ dpm/ml labeled probe. cDNA membranes were washed three times with 2×SSC, 1%SDS for 30 min, once with 0.2×SSC, 0.5% SDS for 30 min, then rinsed in 2×SSC, and exposed to BIOMAX™ MS x-ray film with an intensifying screen (Eastman Kodak Co., Rochester, N.Y., USA). Signal intensities were calculated for individual spots using a STORM-860 phosphor imager (Molecular Dynamics, Sunnyvale, Calif., USA).

Normalized arrays were then hybridized with cDNA probes for genes that have been shown to be involved in cancer. Down-regulation of glutathione peroxidase was previously detected in lung tumors by subtractive hybridization. In fact, matched tumor/normal expression cDNA array reveals the down-regulation of GP in lung tumors of three independent patients. In addition to that, our hybridization data reveal the down-regulation of GP in every one of kidney, breast, and colon tumors. Gelsolin expression has been shown to be down-regulated in human breast ductal carcinoma by immunohistochemistry using a monoclonal antibody. Our matched tumor/normal expression array confirms the down-regulation of GSN in breast tumors, and reveals its down-regulation in prostate, and colon tumors.

These results demonstrate that the SMART PCR-generated cDNA could be beneficial to investigators who only have access to small amounts of tissue, for (i) quick detection of differentially expressed genes between tumor and normal tissues, (ii) to confirm differentially expressed genes identified by other techniques, and (iii) to screen for differentially expressed genes in a large number of independent samples. These experiments demonstrate that SMART cDNA is suitable for high-throughput studies comparing the relative abundance of target genes and for simultaneously detecting differentially expressed genes in a wide variety of tissues.

EXAMPLE 3

Preparation and Use of RNA Chip

The Human RNA Chip provides quick and accurate quantification of mRNA transcripts from a wide variety of tissues and tumor cell lines. It is particularly useful for determining tissue or developmental-stage specificity of gene expression. Easily one can detect whether a gene of interest is broadly expressed in many tissues (such as G3PDH, a housekeeping gene) or if it is tissue-specific (such as TAT, a liver-specific gene). Even low abundant genes (such as lactoferrin, less than 0.001% of an mRNA population) can be observed. Knowing where a gene is expressed gives you insight into the potential function of that's gene's protein. Using two-color fluorescence detection allows performing high-throughput analysis. One can simultaneously hybridize one RNA Chip with two different gene-specific cDNAs, i.e. a housekeeping control cDNA and a gene-specific cDNA. While fluorescent detection has many advantages, radioactive detection can be used as well for highly sensitive expression measurement of low abundant genes.

Pin Spotting of Poly A+ RNAs on a Solid Support 124 human fetal and adult tissue-specific poly A+ RNAs, including 20 RNAs derived from different tumor cell lines are spotted on a solid glass support. The RNAs are spotted in a repeating 6×6 pattern. Within each 6×6 quadrant, spots are approximately 200 um in diameter and are spaced 600 um apart from center to center. The poly A+ RNAs are stably associated with the glass surface through covalent binding. Several methods may be employed for the attachment of nucleic acids, i.e. DNA or RNA, to glass. For example, aliphatic amino groups are introduced to the surface of glass slides by reaction with aminopropyl silane. Poly A+ RNAs pretreated with 10 M sodium isothiocyanate (NaSCN) solution (1:1) are then pin spotted onto the aminopropyl modified glass surface by a Biorobotics printer. The binding occurs through amino-reactive phenylisothiocyanate groups. The poly A+ RNAs are photo-crosslinked to further ensure stable association with the surface of the glass support. Alternatively, an amino derivatized glass surface is coupled to p-phenylenediisothiocyanate (PDC) to convert the amino groups to amino-reactive phenylisothiocyanate groups. Nucleic acids are then reacted with their amino groups and the second isothiocyanate group in PDC to yield surface bound DNA or RNA. The reaction can be carried out in a variety of printing buffers, i.e. 0.5 M sodium carbonate buffer, pH: 9.1, or 0.3M sodium chloride/0.03M sodium citrate, 0.01% SDS (pH: 7.0), or 0.3M lithium chloride/0.03M lithium citrate, 0.01 LiDS (pH: 7.0). After UV-crosslinking either aminopropyl modified or PDC modified glass slides are washed first in 1×SSC, 0.05% SDS (pH:7.0) for 30 sec. and subsequently in 0.6×SSC for another 30 sec. The glass slides are then blocked with sodium borate/succinic anhydride in 1-methyl-2-pyrrolidinone for 15 min. After blocking the slides are transferred to a MilliQ water bath. The slides are incubated for 1 min at 85° C. Finally, the slides are transferred into a container with Ethanol. After 1 min incubation at. room temperature the slides are dried by centrifugation. The slides are now ready for hybridization.

Hybridization, X-ray or Fluorescence Detection

The glass slides with immobilized poly A+ RNAs as described above are incubated with 3.5 ml RNAHyb hybridization solution mixed with either radioactive or fluorescent labeled cDNAs. The hybridization temperature is 50° C. Incubation time is 2–3 hrs. After hybridization the glass slides are washed 3 times for 10 min with 2×SSC, 1% SDS at 65° C., twice for 10 min with 0.1×SSC, 0.5% SDS at 55° C., and 5 times for 1 min with 0.1×SSC at room temperature. After the last wash the slides are dried by centrifugation. Hybridization signals are detected using either a phosphor imager (i.e. STORM, Molecular Dynamics) in the case of emission of radioactive signals or a fluorescence scanner (i.e. AXON, GSI Lumonics) in the case of emission of fluorescent signals.

EXAMPLE 4

Normalization

A. Determination of Reference Ribonucleic Acids for Use in Determining Integral Factor Reference RNAs are selected to carry out the method of the invention. Briefly, a database for housekeeping genes was analyzed for a specific selection criterion. First, the selected ribonucleotides belonging to different functional gene classes were selected to minimize the chance that the reference RNAs will have the same tissue bias. Even housekeeping genes vary in expression between tissues and developmental stages. Although this variation is less pronounced than that of most genes, normalization to the mRNA expression of only one housekeeping gene is suboptimal.

After extensive testing of different genes, each of which are good candidates of reference ribonucleic acids, eight reference ribonucleotides were chosen that provide minimal variation between different tissues and belong to different functional classes. These genes identified and used for subsequent normalization procedures were as follows: ribosomal protein S9, ubiquitin, 23-kDa highly basic protein, HPRT, tubulin, β-actin, phospholipase, and G3PDH. By using eight standards, the small but real variation between tissues of any single difference in mRNA level is de-emphasized.

The selected ribonucleotides were all from single expressed genes and with average transcript sizes between 1–3 kilobases. The average signal for each tissue from the eight standards varies no more than 5-fold from the average of all other tissues.

B. Determination of Levels of Reference RNAs in Each RNA Sample

Oligonucleotide primers, 20–40 base pairs in length, are designed against each of the eight selected reference ribonucleic acids. PCR reactions are carried out to amplify 200–800 bp cDNA probes that would hybridize to each of the selected reference ribonucleic acids. 50 ng of cDNA is radiolabeled with [$^{32}$P]dCTP using standard random primer labeling protocol as described elsewhere (CLONTECH's User Manual, standard procedure) for use as probe.

About 10 ng of 5 different poly A+ RNAs (samples R1 through R5) is spotted on a series of DNA-Ready Type II slides (CLONTECH) and each incubated with 3.5 ml CLONTECH's RNA-Hyb™ solution mixed with a radiolabeled probe that hybridizes to a single reference RNA. The glass slides are incubated with the probe for about 2 hrs. at 50° C. After hybridization the glass slides are washed 3 times with 2×SSC, 1% SDS at 65° C. for 10 min each. Then the glass slides are washed twice with 0.1×SSC, 0.5% SDS at 65° C. for 10 min each. The wash buffer is changed 2–3 times against 0.1×SSC. Finally, the glass slides are washed at room temperature one more time in 0.1×SSC for 10 min. The remaining liquid can be removed by centrifugation. The glass slides are transferred to an X-ray cassette. X-ray exposure is usually overnight at −70° C. The glass slides are phosphorimaged, each dot is quantified and the intensity percentage for each sample is calculated based on the total intensity of all of the signals in all of the samples.

The same procedure is repeated with each of the reference RNA probes on identical glass slides, i.e. glass slides having the same RNA preparation in the same amount on the same relative position on the slide. The percentage (P) results are obtained for each RNA (labeled R1–R5, respectively), and the calculated total value H of each sample calculated, as follows:

|  | R1 | R2 | R3 | R4 | R5 |
|---|---|---|---|---|---|
| Ribosomal Protein S9 | 15 | 21 | 24 | 16 | 24 |
| Ubiquitin | 16 | 21 | 24 | 17 | 22 |
| 23 kD | 14 | 20 | 29 | 17 | 20 |
| HPRT | 15 | 19 | 24 | 19 | 23 |
| Tubulin | 13 | 20 | 28 | 18 | 21 |
| β-actin | 14 | 19 | 26 | 18 | 23 |
| Phospholipase | 16 | 18 | 27 | 17 | 22 |
| GAPDH | 12 | 20 | 28 | 19 | 21 |
| H value | 115 | 158 | 210 | 141 | 176 |

These values are then used to determine an integral factor for each of the samples to determine relative levels between the samples.

C. Determination of an Integral Factor for Each Sample

The calculated H value for each of samples R1 through R5 are used to determine an integral factor (IF) for each of the samples. Sample R2 is used as $IF_{R2}=1$ to determine factors for the rest of the samples:

$IF_{R1}=H_{R2}/H_{R1}=158/115=1.37$ $IF_{R2}=H_{R2}/H_{R2}=1$ $IF_{R3}=H_{R2}/H_{R3}=158/210=0.71$ $IF_{R4}=H_{R2}/H_{R4}=158/141=1.12$ $IF_{R5}=H_{R2}/H_{R5}=158/176=0.9$

These integral factors can be used to compare relative levels between these samples on any array having these samples.

D. Normalization of Detection Levels on an Array

Each of the five poly(A)+ RNA samples, R1–R5, is spotted onto a glass slide. The amounts of sample loaded are as follows: 2 μg sample R1; 2 μg sample R2; 10 μg sample R3; 5 μg sample R4; and 0.5 μg sample R5. A cDNA probe against probe against a sequence of interest is generated via PCR, and radiolabeled with [$^{32}$P]dCTP for detection. The glass slide and the probe are incubated with 3.5 ml CLONTECH's ExpressHyb solution mixed with a radiolabeled probe that hybridizes to a single reference ribonucleotide. The glass slides are incubated with the probe for about 2 hrs. at 50° C. After hybridization the glass slides are washed 3 times with 2×SSC, 1% SDS at 65° C. for 10 min each. Then the glass slides are washed twice with 0.1×SSC, 0.5% SDS at 65° C. for 10 min each. The washbuffer is changed 2–3 times against 0.1×SSC. Finally, the glass slides are washed at room temperature one more time in 0.1×SSC for 10 min. The remaining liquid can be removed by centrifugation. The glass slides are transferred to an X-ray cassette. X-ray exposure is usually overnight at −70° C. The glass slides were phosphoimaged, and the phosphor imager signal of each dot is quantified. Results are as follows:

$S_{R1}=1,000$ $S_{R2}=1,500$ $S_{R3}=3,000$ $S_{R4}=1,500$ $S_{R5}=500$

The relative amount of each sample can now be determined based on the levels of the sample on the slide and the integral factor for each sample. First, all of the signals are determined on a per microgram basis:

$S_{R1}=1,000 \div 2=500/\mu g$ $S_{R2}=1,500 \div 2=750/\mu g$ $S_{R3}=3,000 \div 10=300/\mu g$ $S_{R4}=1,500 \div 5=300/\mu g$ $S_{R5}=500 \div 0.5=1,000/\mu g$ Once the per gram basis has been calculated, each level is multiplied by its integral factor to determine the relative levels of the transcript of interest in each sample/microgram of poly A+ mRNA:

$S_{R1}=500/\mu g \times 1.37=685$ $S_{R2}=750/\mu g \times 1=750$ $S_{R3}=300/\mu g \times 0.71=213$ $S_{R4}=300/\mu g \times 1.12=336$ $S_{R5}=1000/\mu g \times 0.90=900$ As can be seen from the "normalized" amounts, the transcript of interest displays lower expression in samples R3 and R4, and elevated levels of expression in R5. Thus, although the phosphor imager signal of R5 was the lowest on the slide, the calculations show that this sample actually has the highest relative level of transcript.

It is evident from the above results and discussion that the subject arrays provide for improved methodologies in gene expression analysis applications. The subject arrays are capable of being premade and then used in assays at a later date and by a different user, thereby saving the assay performer from having to go through the preparation of the array at the time of use. Since the subject arrays can be pre-prepared, they can be mass produced under uniform specifications, thereby assuring comparability of results obtained using the subject devices. Furthermore, since the subject arrays comprise a solid support, they are particularly suited for use in high throughput analyses and with automated devices, such as fluid handling devices, readers and the like. The subject arrays can be fabricated in such a way as to readily usable with standard detection devices currently employed by those in the relevant fields. The subject arrays provide a convenient means of assaying the expression of a particular gene of interest in a large number of different tissues simultaneously, where the individual tissues may be difficult to individually produce. As such, the subject invention represents a significant contribution to the art.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. An array of a plurality of different heterogeneous polymeric target compositions immobilized on a surface of a solid support, wherein said array is further characterized by at least one of the following features:
   (a) said solid support is rigid; and
   (b) said plurality of different heterogeneous polymeric target compositions includes at least one normal/disease pair of heterogeneous polymeric target compositions,
   wherein each heterogeneous polymeric target composition is made up of at least about 100 different molecules.

2. The array according to claim 1, wherein said heterogeneous polymeric target compositions are made up of polymeric target constituents selected from the group consisting of nucleic acids and peptides.

3. The array according to claim 2, wherein said polymeric constituents are nucleic acids.

4. The array according to claim 3, wherein said nucleic acids are ribonucleic acids.

5. The array according to claim 4, wherein said ribonucleic acids are polyA+RNA.

6. The array according to claim 3, wherein said nucleic acids are deoxyribonucleic acids.

7. The array according to claim 3, wherein said polymeric target compositions comprise normalized amounts of nucleic acids.

8. The array according to claim 2, wherein said polymeric constituents are covalently bonded to said surface.

9. The array according to claim 2, wherein said polymeric constituents are non-covalently associated with said surface.

10. The array according to claim 1, wherein said rigid solid support is glass.

11. The array according to claim 1, wherein said normal/disease pair of polymeric target compositions is made up of a first polymeric target composition derived from a normal sample and a second polymeric target composition derived from a disease sample.

12. The array according to claim 11, wherein said normal/disease pair of polymeric target compositions comprises a plurality of target compositions each derived from a different disease sample.

13. The array according to claim 1, wherein said solid support is rigid and said polymeric target compositions are made up of nucleic acids.

14. The array according to claim 13, wherein said rigid solid support is glass.

15. The array according to claim 14, wherein said normal/disease pair of polymeric target compositions is made up of a first polymeric target composition derived from a normal sample and a second polymeric target composition derived from a disease sample.

16. A kit for use in a method of detecting a binding event between a probe and target, said kit comprising:
   an array according to claim 13.

17. The array according to claim 14, wherein said normal/disease pair of polymeric target compositions comprises a plurality of target compositions each derived from a different disease sample.

18. The array according to claim 1, wherein the density of said different polymeric target compositions on the surface of said array is at least about 10/cm$^2$.

19. A method for detecting a binding event between a probe and target compound, said method comprising:
   contacting a probe comprising solution with an array according to claim 1; and
   detecting a binding event between at least one of said polymeric targets and said probe.

20. The method according to claim 19, wherein said probe is labeled and said detecting comprises detecting the presence of said label.

21. The method according to claim 20, wherein said label is selected from the group consisting of isotopic, fluorescent and enzymatic labels.

22. The method according to claim 19, wherein said method further comprises washing said substrate of unbound probe prior to said detecting.

23. The method according to claim 19, wherein said binding event is between members of a specific binding pair.

24. The method according to claim 23, wherein said members are peptides.

25. The method according to claim 23, wherein said binding event comprises hybridization between complementary nucleic acids.

26. The method according to claim 19, wherein said array is contacted with two different probes that are distinguishably labeled.

27. A kit for use in a method of detecting a binding event between a probe and target, said kit comprising:
   an array according to claim 1.

28. The kit according to claim 27, wherein said kit further comprises one or more members of a labeled probe generation system.

29. The kit according to claim 27, wherein said kit further comprises at least one buffer medium.

30. The kit according to claim 27, wherein said kit further comprises at least one control probe.

31. The kit according to claim 30, wherein said control probe is labeled.

* * * * *